(12) United States Patent
Dellanina

(10) Patent No.: US 7,114,950 B2
(45) Date of Patent: Oct. 3, 2006

(54) DENTAL HYGIENE DEVICE AND TEETH POLISHING METHOD

(76) Inventor: Gina Dellanina, 2233 Martin, #412, Irvine, CA (US) 92612

( * ) Notice: Subject to any disclaimer, the term of this patent is extended or adjusted under 35 U.S.C. 154(b) by 273 days.

(21) Appl. No.: 10/757,362

(22) Filed: Jan. 14, 2004

(65) Prior Publication Data

US 2004/0185416 A1 Sep. 23, 2004

Related U.S. Application Data

(60) Provisional application No. 60/440,134, filed on Jan. 15, 2003.

(51) Int. Cl.
*A61C 3/00* (2006.01)
(52) U.S. Cl. .................... 433/163; 433/91; 433/49
(58) Field of Classification Search .............. 433/49, 433/50, 77, 79, 163, 91
See application file for complete search history.

(56) References Cited

U.S. PATENT DOCUMENTS

| | | | | |
|---|---|---|---|---|
| 2,665,479 A | * | 1/1954 | Weldon | 433/163 |
| 3,327,391 A | * | 6/1967 | Malm | 433/163 |
| 4,717,057 A | * | 1/1988 | Porteous | 224/217 |
| 5,016,795 A | * | 5/1991 | Porteous | 224/217 |
| 5,048,731 A | * | 9/1991 | Moreschini | 433/163 |
| 5,112,227 A | * | 5/1992 | Bull | 433/163 |
| 5,169,315 A | * | 12/1992 | Bull | 433/163 |
| 5,441,410 A | * | 8/1995 | Segerdal | 433/93 |
| 5,732,862 A | * | 3/1998 | Bull | 224/217 |
| 6,280,189 B1 | * | 8/2001 | Muller | 433/49 |

OTHER PUBLICATIONS

Copy of NUPRO Prophylaxis Paste, With Fluoride And Without Fluoride Sep. 1998.

* cited by examiner

*Primary Examiner*—Ralph A. Lewis
(74) *Attorney, Agent, or Firm*—John J. Connors; Connors & Assoc. Inc.

(57) ABSTRACT

A dental hygiene device comprises a cup member including an attachment member that enables the device to be attached and detached to a suction tube adapted to be inserted into the mouth of a patient during polishing of the patient's teeth. The cup member holds a tooth polishing material that is accessed by a dental hygienist during polishing of a patient's teeth.

12 Claims, 2 Drawing Sheets

DENTAL HYGIENE DEVICE AND TEETH POLISHING METHOD

RELATED PATENT APPLICATIONS & INCORPORATION BY REFERENCE

This application is a utility application based on U.S. provisional patent application Ser. No. 60/440,134, entitled "Prophy Cup Attachment," filed Jan. 15, 2003. This related application is incorporated herein by reference and made a part of this application. If any conflict arises between the disclosure of the invention in this utility application and that in the related provisional application, the disclosure in this utility application shall govern. Moreover, the inventor incorporates herein by reference any and all U.S. patents, U.S. patent applications, and other documents cited or referred to in this application or cited or referred to in the U.S. patents and U.S. patent applications incorporated herein by reference.

DEFINITIONS

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

BACKGROUND OF INVENTION

Polishing teeth is a common dental procedure wherein a polishing material is applied to a patient's teeth using an implement attached to the handpiece of a dental drill. The polishing implement, commonly referred to as a prophy angle, is periodically tipped into a container of polishing material to collect on the tip of the implement some of this material. The tip of the implement with the material thereon is then brought to bear against a tooth of the patient.

SUMMARY OF INVENTION

This invention has one or more features as discussed subsequently herein. After reading the following section entitled "DETAILED DESCRIPTION OF ONE EMBODIMENT OF THIS INVENTION," one will understand how the features of this invention provide its benefits. The benefits of this invention include, but are not limited to: convenience of use, improved ergonomics for the user polishing teeth, reduction of saliva flow for a drier working environment, improved patient comfort, more effective use of polishing material, reduction in the time to polish teeth, low cost, and disposability.

Briefly, this invention comprises a cup member that holds the polishing material and an attachment member such as a clip incorporated into the cup member that attaches to a suction tube, commonly referred to as a saliva ejector in a dental operatory. The suction tube is placed in the patient's mouth at the time of polishing.

This invention saves time, decreases frustration of the user, typically a dental hygienist, and helps keep an ideal dry environment for the user while providing the service of polishing the patient's teeth. While the user polishes the patient's teeth excess saliva can be produced which can decrease the effect of the polish and increase patient discomfort caused by pooling saliva in the patient's mouth (it is best to polish in an dry environment so the polishing material can effectively remove soft plaque etc. and clean the tooth surface). When employing the conventional polishing method, the user has to stop several times to suction out the saliva to keep the mouth dry and the patient comfortable. That means stopping the polishing procedure, putting down the polishing implement and the container of the polishing material, and picking up and placing the suction tube in the patient's mouth to remove the pooling saliva. This takes up time as well as gets messy for the patient and the user. This invention avoids stopping polishing in order to apply suction to keep the mouth dry. This enables the user to access to the polishing material while allowing suction to be used continuously so the mouth can stay dry, the patient can remain comfortable, and allows the user to save time and not be inconvenienced.

Without limiting the scope of this invention as expressed by the claims that follow, some, but not necessarily all, of its features are:

One, the dental hygiene device of this invention includes a cup member with a compartment holding a tooth polishing material and an attachment member that enables the device to be attached and detached to a suction tube adapted to be inserted into the mouth of a patient during polishing of the patient's teeth. The compartment may hold a sufficient amount of polishing material to polish the teeth of essentially only a single patient. The device may be molded from a plastic. The cup member has an open top covered with a removable seal and a closed bottom. The attachment member may project outwardly from the closed bottom.

Two, the attachment member may comprise a pair of finger elements of sufficient length and spaced apart a predetermined distance so that, upon inserting the tube between the finger elements, the device is held securely to the tube during polishing of the patient's teeth. The finger elements may be centrally located, are substantially parallel, and are substantially parallel to a longitudinal axis of the cup member. The finger elements may merge at a base member connected to the bottom and form an open bite having a substantially circular configuration having a diameter slightly less than a diameter of the suction tube. The finger elements may have inner edges tapering outward from the open bite to terminate at ends spaced apart a distance slightly greater than the diameter of the suction tube.

These features are not listed in any rank order nor is this list intended to be exhaustive.

This invention also includes a method polishing teeth. In accordance with the method of this invention a suction tube is placed into an open mouth of a patient, this tube having a dental hygiene device mounted on the tube nearby the open mouth and the dental hygiene device holds a tooth polishing material that is accessed periodically during polishing of the patient's teeth.

DESCRIPTION OF DRAWING

One embodiment of this invention, illustrating all its features, will now be discussed in detail. This embodiment depicts the novel and non-obvious dental hygiene device and teeth polishing method of this invention as shown in the accompanying drawing, which is for illustrative purposes only. This drawing includes the following figures (Figs.), with like numerals indicating like parts.

DETAILED DESCRIPTION OF ONE EMBODIMENT OF THIS INVENTION

Figure 1:
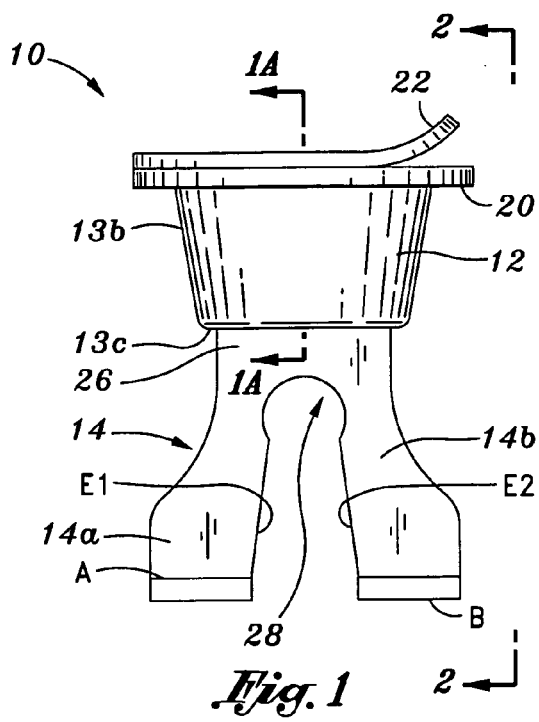
FIG. 1 is a side elevational view of one embodiment of the dental hygiene device of this invention.
Figure 1A:
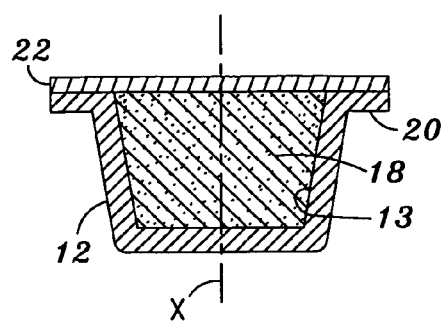
FIG. 1A is a cross-sectional view taken along line 1A—1A of FIG. 1.
Figure 2:
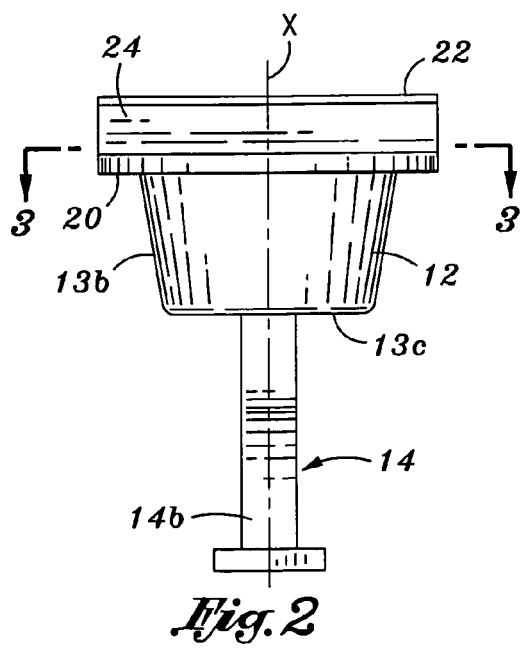
FIG. 2 is a front elevational view of the dental hygiene device of this invention taken along line 2—2 of FIG. 1.
Figure 3:
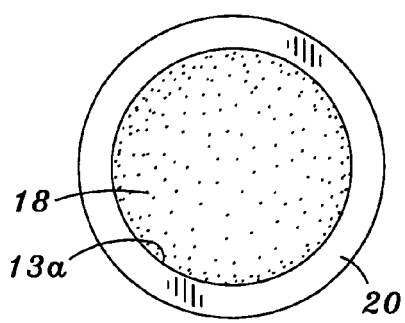
FIG. 3 is a cross-sectional view taken along line 3—3 of FIG. 2.
Figure 4:
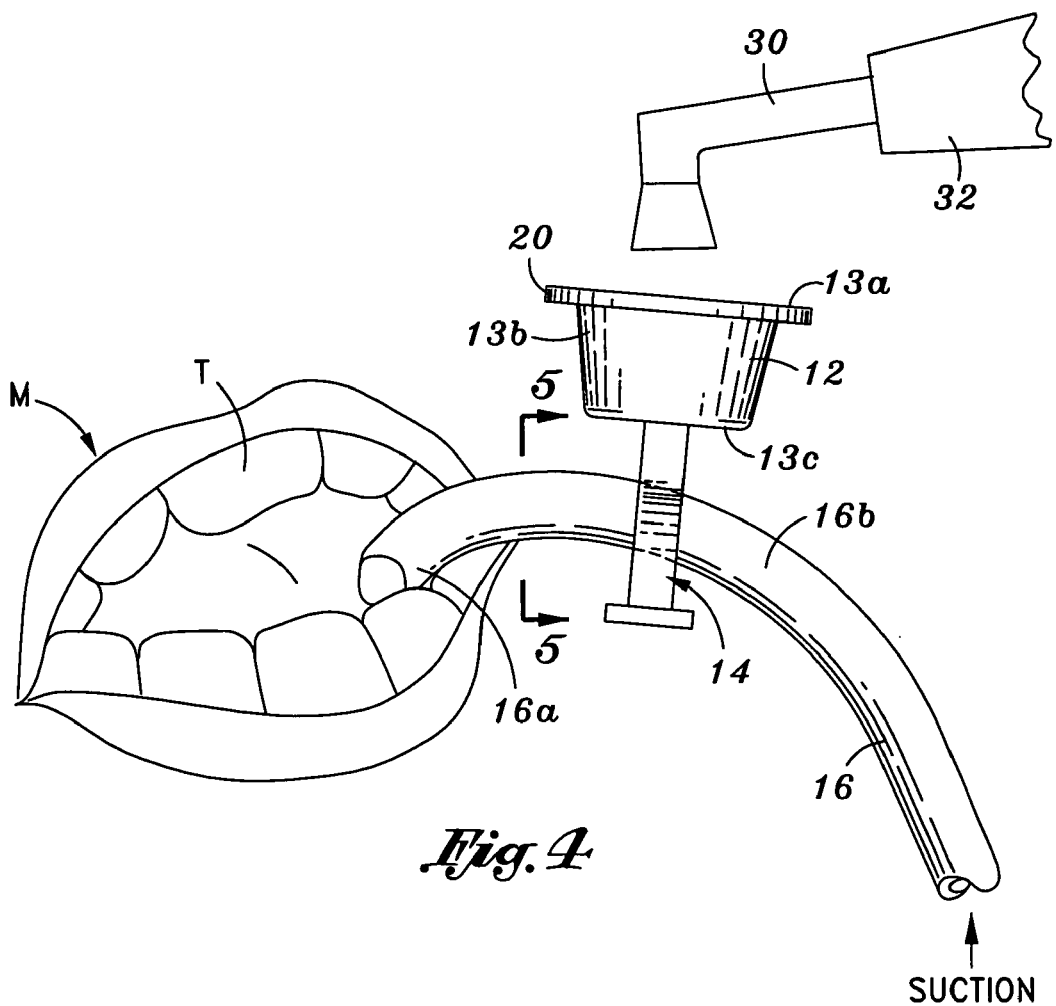
FIG. 4 is a perspective view illustrating using the one embodiment of the dental hygiene device of this invention shown in FIGS. 1 through 3.

As depicted in FIGS. 1 through 3, one embodiment of this invention, the dental hygiene device 10, includes a cup member 12 having an attachment member 14 that enables the device to be attached and detached to a suction tube 16 (FIG. 4). This suction tube 16, the saliva ejector, is adapted to be inserted into the mouth M (FIG. 4) of a patient during polishing of the patient's teeth T. The cup member 12 holds within an internal compartment 13 (FIG. 1A) a tooth polishing material 18 such as, for example, Nupro® prophylaxis paste manufactured by DENTSPLY Preventive Care of York Pa. This polishing material 18 is a moist paste comprising an abrasive material including solid particulates. The device 10 may be molded from a plastic such as, for example polypropylene, to form a unitary structure with the cup member 12 and the attachment member 14 integrated as a single piece.

The compartment 13 is filled with a sufficient amount of polishing material 18 to polish the teeth T of essentially only a single patient. For example, in the embodiment illustrated the compartment 13 has the capacity to hold from about 0.05 to about 0.1 cubic inches of the tooth polishing material 18. This compartment 13 has an open top 13a, a substantially cylindrical side wall 13b, and a closed bottom 13c. The open top 13a has a substantially circular configuration and is at least partially encompassed by a rim 20 that projects outwardly from a side wall 13b of the cup member 12 at an angle of about 90° with respect to the longitudinal axis X of the cup member 12. A removable seal 22, shown partially removed, covers and seals the open top 13a and prevent access to the polishing material 18 until the user is ready to polish a patent's teeth. This seal may be a thin foil material with an adhesive 24 (FIG. 2) between the rim and perimeter of the seal fixing the seal 20 to the rim 20 until removed.

The attachment member 14 projects outwardly from the bottom wall 13c of the cup member 12 and it may be in the form of a clip configured to grasp the suction tube 16. The attachment member 14 may comprise a pair of fingers 14a and 14b. The fingers 14a and 14b are of sufficient length and spaced apart a predetermined distance so that upon inserting the suction tube 16 (FIG. 5) between the fingers the device 10 is held securely to the tube during polishing of the patient's teeth with the fingers straddling and grasping the tube. The fingers 14a and 14b are centrally located, are substantially parallel, and are substantially parallel to the longitudinal axis X of the cup member 12. These finger elements 14a and 14b merge at a base member 26 connected to the bottom wall 13c and form an open bite 28 (FIG. 1) having a substantially circular configuration having a diameter slightly less than the diameter of the suction tube 16, for example, the diameter of the open bite 28 may be substantially about 0.25 inch. The fingers 14a and 14b each have inner edges E1 and E2 tapering outward from the open bite 28 to terminate at ends A and B spaced apart a distance slightly greater than the diameter of the suction tube 16. The inner edges each tapers outward from the bottom wall 13c at an angle from about 1 to about 10° with respect to the longitudinal axis X of the cup member 12.

Figure 5:
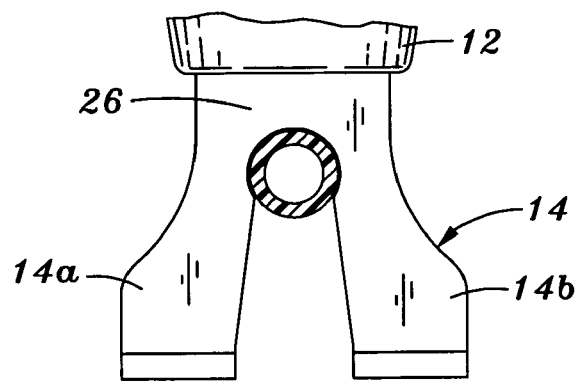
FIG. 5 is a cross-sectional view taken along line 5—5 of FIG. 4.

In accordance with the teeth polishing method of this invention the device 10 is attached to the suction tube 16 and then detached and disposed of after using. As best illustrated in FIG. 5, an end 16a of a suction tube 16 is placed into an open mouth M of a patient with an adjacent portion 16b of the tube extending from the open mouth. With the device 10 mounted on the adjacent portion 16b of the tube 16 by the attachment member 14, the cup member 12 is positioned on the tube 16 to enable access to the tooth polishing material 18 during polishing of the patient's teeth. A conventional disposable polishing implement 30 connected to a conventional dental handpiece 32 of a dental drill (not shown) is used to apply the polishing material 18 from the cup member 12 to the teeth T. A suitable polishing implement 30 is sold by DENTSPLY Preventive Care of York Pa. identified as the prophy angle bearing the trademark Rite-Angle®. The patient's teeth T are polished while suction is concurrently being applied through the suction tube 16 to withdraw saliva from the patient's mouth. The polishing implement 30 is periodically inserted by the user into the tooth polishing material 18 to collect on the implement a portion of the material in the cup member 12. When all the patient's teeth are polished, the compartment 13 is essentially depleted of all the polishing material 18 and the device 10 is detached from the tube 16 and discarded.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention.

The invention claimed is:

1. A method of polishing teeth comprising
   (a) placing an end of a suction tube into an open mouth of a patient with an adjacent portion of the tube extending from the open mouth,
   (b) mounting on the adjacent portion of the tube a dental hygiene device including an attachment member that enables the device to be attached and detached to the suction tube and a cup member holding a tooth polishing material, said device positioned on the tube to enable access to the tooth polishing material during polishing of the patient's teeth, and
   (c) polishing the patient's teeth using a polishing implement connected to a tip of a dental handpiece while suction is concurrently being applied through said tube to withdraw saliva from the patient's mouth, said polishing implement being periodically inserted into the tooth polishing material to collect on the implement a portion of the material in the cup.

2. The method of claim 1 where the attachment member is substantially in the form of a clip member.

3. A method of polishing teeth where a suction tube is placed into an open mouth of a patient, said tube having a dental hygiene device mounted on the tube nearby the open mouth, said dental hygiene device holding a tooth polishing material that is accessed periodically during polishing of the patient's teeth.

4. A dental hygiene device adapted to be attached and detached to a suction tube inserted into the mouth of a patient during polishing of the patient's teeth, said tube having a predetermined diameter, said device comprising a cup member holding only a sufficient amount of polishing material to polish the teeth of essentially only a single patient, said cup member having an open top covered with a removable seal and a closed bottom wall, a clip configured to grasp the tube and including a pair of finger elements extending outward from the bottom wall that straddle a longitudinal axis of the cup member, said fingers having spaced apart, outer terminal ends and inner ends that merge nearby the bottom wall to form between said inner ends an open bite that has a predetermined open dimension that is slightly less than the diameter of the suction tube, said finger elements having inner edges tapering outward from the open bite to terminate at said outer ends, said outer ends being spaced apart a distance slightly greater than the diameter of the open bite so that the tube passes between the outer ends and into the open bite to detachably connect the clip to the tube.

5. The dental hygiene device of claim 4 where the open bite has a substantially circular configuration.

6. The dental hygiene device of claim 5 where the diameter of the open bite is substantially 0.25 inch.

7. The dental hygiene device of claim 4 where the inner edges each tapers outward from the bottom wall at an angle substantially from 1 to 10 degrees with respect to the longitudinal axis of the cup member.

8. The dental hygiene device of claim 4 where the cup member has a volume substantially from 0.05 to 0.1 cubic inch.

9. The dental hygiene device of claim 4 is molded from plastic.

10. A dental hygiene device adapted to be attached and detached to a suction tube inserted into the mouth of a patient during polishing of the patient's teeth, said device being molded from a plastic and comprising a cup member having a volume substantially from 0.05 to 0.1 cubic inch and holding only a sufficient amount of polishing material to polish the teeth of essentially only a single patient, said cup member having an open top covered with a removable seal and a closed bottom wall, a clip configured to grasp the tube and including a pair of finger elements extending outward from the bottom wall that straddle a longitudinal axis of the cup member, said fingers having spaced apart, outer terminal ends and inner ends nearby the bottom wall to form between said inner ends an open bite having a substantially circular configuration with a diameter of substantially 0.25 inch, said finger elements having inner edges tapering outward from the open bite to terminate at said outer ends, said outer ends being spaced apart a distance slightly greater than the diameter of the open bite so that the tube passes between the outer ends and into the open bite to detachably connect the clip to the tube.

11. The dental hygiene device of claim 10 where the inner edges each tapers outward from the bottom wall at an angle substantially from 1 to 10 degrees with respect to the longitudinal axis of the cup member.

12. The combination comprising a suction tube adapted to be inserted into the mouth of a patient and a dental hygiene device detachably connected to a portion of the suction tube extending from the mouth of the patient, said dental hygiene device comprising a cup member holding a tooth polishing material, said cup member having a bottom including an outwardly projecting attachment member connected to the suction tube during polishing of the patient's teeth.

* * * * *